United States Patent [19]

Buxadé

[11] Patent Number: 4,960,917
[45] Date of Patent: Oct. 2, 1990

[54] PROCESS FOR THE PREPARATION OF AN ACEXAMIC ACID DERIVATIVES

[75] Inventor: Antonio Buxadé, Barcelona, Spain

[73] Assignee: Laboratorios Vinas, S.A., Barcelona, Spain

[21] Appl. No.: 455,638

[22] Filed: Dec. 22, 1989

[30] Foreign Application Priority Data

Dec. 26, 1988 [ES] Spain ................................. 8803957

[51] Int. Cl.$^5$ .............................................. C07F 7/06
[52] U.S. Cl. ................................................... 556/131
[58] Field of Search ............................. 556/131, 118

[56] References Cited

U.S. PATENT DOCUMENTS

| | | | |
|---|---|---|---|
| 3,917,722 | 11/1975 | Yates | 556/131 X |
| 4,302,573 | 11/1981 | Stockinger et al. | 556/131 X |
| 4,425,278 | 1/1984 | Wirth et al. | 556/131 X |
| 4,590,255 | 5/1986 | O'Connor et al. | 556/131 X |

Primary Examiner—Arthur C. Prescott
Attorney, Agent, or Firm—Michael J. Striker

[57] ABSTRACT

This process for the preparation of an acexamic acid derivative, namely the zinc salt of formula:

$$(CH_3-CONH-(CH_2)_5-COO)_2Zn$$

comprises reacting the acexamic acid with zinc hydroxide in a polar solvent. It finds application in the manufacture of compounds having antiulcer properties.

5 Claims, No Drawings

PROCESS FOR THE PREPARATION OF AN ACEXAMIC ACID DERIVATIVES

FIELD OF THE INVENTION

The present invention relates to a process for the preparation of an acexamic acid derivative, namely the zinc salt of that acid.

This salt, of formula $(CH_3-CONH-(CH_2)_5-COO)_2Zn$ has antiulcer properties.

BACKGROUND OF THE INVENTION

Zinc salts have been prepared up to now, among other methods, by using reactants such as basic zinc carbonate or zinc carbonate, which were reacted directly with the corresponding acid with the advantage, in compounds for pharmaceutical use, of avoiding the presence, as contaminants, of other anions (sulfates, chlorides, etc ) derived from the prior preparation of the sodium or potassium salts, followed by subsequent reaction with zinc sulfate, zinc chloride, etc., respectively. Nevertheless, these carbonates have the drawback, in their most obtainable commercial form, of lack of homogeneity and varying composition, which is even more noticeable when they are to be reacted with weak organic acids, making the purification of the end product to improve its quality more elaborate.

SUMMARY OF THE INVENTION

To overcome the above drawbacks, research has been directed to the development of new operative methods and it has been discovered that when zinc hydroxide, a homogenous product having a defined composition, is used, the end product may be produced not only with the absence of other contaminating anions, but also with a superior quality, not needing additional manipulation.

Accordingly, in the process of my invention equimolar amounts of acexamic acid and zinc hydroxide, or a slight excess of the former, are reacted in a polar solvent or mixture of solvents, preferably water.

The temperature may be up to the boiling point of the solvent, advantageously a temperature lying between 80° and 90° C. is used.

The acid may first be dissolved in the solvent, with the zinc hydroxide being added portionwise or in slurry or suspension form once the reaction temperature has been reached. Also, a suspension mixture of acid and hydroxide may be prepared in the solvent, followed by heating to reaction temperature.

The salt may be isolated by crystallisation in the same solvent, or by adding another solvent in which it is less soluble, to increase the yield. The product is finally filtered and dried.

EXAMPLES OF THE INVENTION

To facilitate the explanation, the invention is illustrated by, but not limited to, the following Examples:

EXAMPLE 1

3.46 g (20 mmoles) of acexamic acid were dissolved in 8 ml of distilled water. The solution was heated to 90° C. and a slurry formed by 0.99 g (10 mmoles) of zinc hydroxide was gradually added.

After the addition was over, the mixture was allowed to react with stirring for 15 minutes at that temperature, after which it was allowed to cool to room temperature. Thereafter it was cooled to 5° C. It was allowed to rest for 12 hours at this temperature, was filtered, washed and dried at 60° C.

In this way, a white crystalline powder, zinc acexamate was obtained.

Melting point: 193°–196° C.

Elementary analysis for $C_{16}H_{26}N_2O_6Zn$:

|  | C | H | N | Zn |
|---|---|---|---|---|
| Calculated (%) | 46.94 | 6.84 | 6.84 | 15.96 |
| Found (%) | 47.08 | 6.95 | 6.80 | 15.85 |

EXAMPLE 2

3.46 g (20 mmoles) of acexamic acid and 0.99 g (10 mmoles) of zinc hydroxide were poured into a flask containing 10 ml of distilled water. The temperature was raised to 90° C. and held for 30 minutes. The mixture was allowed to cool to room temperature and was thereafter cooled to 5° C. It was allowed to stand at that temperature for 12 hours, was filtered, washed and dried at 60° C.

In this way a white crystalline powder having the same characteristics as the one obtained following Example 1 was obtained.

While the invention has been illustrated and described as embodied in a process for preparation of a new tryptophane derivative, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention. What is claimed as new and desired to be protected by Letters Patent is set forth in the appended claims.

What is claimed is:

1. A process for preparation of an acexamic acid derivative, namely the zinc salt of formula:

$(CH_3-CONH-(CH_2)_5-COO)_2Zn$ comprising the step of reacting acexamic acid with zinc hydroxide in a polar solvent.

2. The process of claim 1, wherein said solvent is water.

3. The process of claim 1, in which said reacting occurs at a reaction temperature equal to a boiling point temperature of said solvent.

4. The process of claim 1, in which said reacting occurs at a reaction temperature lower than a boiling point temperature of said solvent.

5. The process of claim 1, further comprising the steps of isolating said zinc salt by crystallization in said solvent, filtering and drying.

* * * * *

UNITED STATES PATENT AND TRADEMARK OFFICE
CERTIFICATE OF CORRECTION

PATENT NO. : 4,960,917
DATED : October 2, 1990
INVENTOR(S) : Antonio Buxade

It is certified that error appears in the above-identified patent and that said Letters Patent is hereby corrected as shown below:

In Column 2, lines 32 to 46, delete lines 32 to 46.

Signed and Sealed this

Twenty-fifth Day of August, 1992

*Attest:*

DOUGLAS B. COMER

*Attesting Officer*            Acting Commissioner of Patents and Trademarks